(12) United States Patent
Eggen et al.

(10) Patent No.: US 6,840,092 B2
(45) Date of Patent: Jan. 11, 2005

(54) METHOD AND APPARATUS FOR RHEOMETRY, AND ITS APPLICATION TO CONTROL OF POLYMER MANUFACTURE

(75) Inventors: Svein Eggen, Eidanger (NO); Petter Asrud, Porsgrunn (NO)

(73) Assignee: Borealis Technology Oy, Porvoo (FI)

( * ) Notice: Subject to any disclaimer, the term of this patent is extended or adjusted under 35 U.S.C. 154(b) by 0 days.

(21) Appl. No.: 10/182,679

(22) PCT Filed: Jan. 31, 2001

(86) PCT No.: PCT/GB01/00406

§ 371 (c)(1),
(2), (4) Date: Nov. 8, 2002

(87) PCT Pub. No.: WO01/57492

PCT Pub. Date: Aug. 9, 2001

(65) Prior Publication Data

US 2003/0140682 A1 Jul. 31, 2003

(30) Foreign Application Priority Data

Jan. 31, 2000 (GB) .............................. 0002192

(51) Int. Cl.[7] .............................................. G01N 11/04
(52) U.S. Cl. .................... 73/54.11; 73/53.01; 73/54.09; 73/54.01; 73/64.54
(58) Field of Search ............................. 73/54.11, 53.01, 73/54.09, 64.54, 54.01

(56) References Cited

U.S. PATENT DOCUMENTS

| | | | | |
|---|---|---|---|---|
| 3,048,030 A | * | 8/1962 | De Haven ........................ 73/56 |
| 3,420,096 A | * | 1/1969 | Hoyt ............................... 73/54 |
| 3,839,901 A | * | 10/1974 | Finkle et al. ..................... 73/54 |
| 4,138,194 A | * | 2/1979 | Beasley et al. ............. 350/96.3 |
| 4,241,602 A | * | 12/1980 | Han et al. .................... 73/54.14 |
| 4,316,383 A | * | 2/1982 | Frruman et al. ................ 73/55 |
| 4,425,790 A | | 1/1984 | Bice et al. ....................... 73/55 |
| 4,448,736 A | | 5/1984 | Emery et al. ................ 264/40.1 |
| 4,449,395 A | * | 5/1984 | Kurtz et al. .................... 73/56 |
| 4,500,687 A | * | 2/1985 | Wolfe .......................... 525/412 |
| 4,539,837 A | | 9/1985 | Barnaby ......................... 73/55 |
| 4,573,345 A | | 3/1986 | Krutchen et al. ............... 73/56 |
| 4,754,413 A | | 6/1988 | Köster et al. ................ 364/473 |
| 4,821,564 A | * | 4/1989 | Pearson et al. ................ 73/155 |
| 4,858,127 A | * | 8/1989 | Kron et al. ............. 364/413.07 |
| 4,882,930 A | * | 11/1989 | Nagy et al. ..................... 73/56 |
| 5,014,545 A | * | 5/1991 | Rao ................................ 73/55 |
| 5,347,852 A | | 9/1994 | Mode ......................... 73/54.04 |
| 5,459,677 A | | 10/1995 | Kowalski et al. ........ 364/571.02 |
| 5,527,858 A | * | 6/1996 | Blong et al. .................. 526/352 |
| 5,559,728 A | | 9/1996 | Kowalski et al. ........ 364/571.02 |
| 5,652,376 A | * | 7/1997 | Deleeuw et al. ............ 73/54.36 |
| 5,688,457 A | * | 11/1997 | Buckmaster et al. ......... 264/211 |
| 5,847,267 A | * | 12/1998 | Janzen ....................... 73/54.01 |
| 6,046,051 A | * | 4/2000 | Jina .............................. 436/69 |
| 6,060,323 A | * | 5/2000 | Jina .............................. 436/69 |
| 6,114,486 A | * | 9/2000 | Rowland et al. ............. 526/352 |
| 6,261,244 B1 | * | 7/2001 | Kensey et al. ............... 600/573 |

FOREIGN PATENT DOCUMENTS

| | | | | |
|---|---|---|---|---|
| EP | 0 238 796 A2 | 9/1987 | ........... B29C/47/92 |
| EP | 0 595 276 A3 | 5/1994 | ........... G01N/11/08 |
| GB | 2 158 252 | 11/1985 | ........... G01N/11/04 |

OTHER PUBLICATIONS

Baker et al, "Efficient integration boosts on–line rheometer benefits", Modern Plastics International, May, 1997, pp. 123–126; XP–000721670.

Gleissle, "Rheological Measurements for Quality and Process Control", Rheology 95, Mar. 1995, pp. 14–23.

Baker et al; "Efficient Integration Boosts On–Line Heometer Benefits" Modern Plastics International, CH, McGraw–Hill, Inc. Lausanne, vol. 27, No. 5, May 1, 1997, pp. 123–124, 126; XP000721670.

* cited by examiner

Primary Examiner—Hezron Williams
Assistant Examiner—Rodney Frank
(74) Attorney, Agent, or Firm—Nixon & Vanderhye, PC (57) ABSTRACT

A method and apparatus for studying the properties of a fluid are provided in which in which a rheometer is used to obtain, for example, value(s) indicative of the shear stress in the fluid to thereby obtain a set of data. The data is then directly compared using, for example, multivariate analysis, with previously obtained data corresponding to a fluid(s) with known rheological properties. The results of this comparison can then be used, for example, to control a manufacturing process.

27 Claims, 7 Drawing Sheets

METHOD AND APPARATUS FOR RHEOMETRY, AND ITS APPLICATION TO CONTROL OF POLYMER MANUFACTURE

This application is the US national phase of international application PCT/GB01/00406 filed Jan. 31, 2001, which designated the US.

The present invention relates to a method of rheometry and to a corresponding rheometer apparatus. The invention is of particular, but not exclusive, application to the manufacturing of polymers.

Rheometry is the study of the characteristics of non-Newtonian fluids. These are fluids in which viscosity is not independent of rate of shear.

Common examples of such fluids are the molten polymers which are found in polymer manufacturing plants. In such a plant the basic polymer is formed in a reactor which generally produces it in powder form. The powder may then undergo further processing steps such as degassing before it is fed to an extruder. In the extruder, the powder is melted and then extruded into a suitable form for delivery, for example as pellets.

In order to monitor the characteristics of such fluids, devices known as rheometers are used. The data thereby obtained, such as an estimate of the melt flow rate of the molten polymer, can be used to assist in monitoring the operation of the plant. Commonly the instrument is arranged such that material is transported to it automatically from the plant process steam, in which case it is termed an on-line rheometer. The terms "in-line" and "at-line" are also used.

The melt flow rate (MFR) is the rate of flow (in terms of mass per unit time) of molten polymer through a die of known dimensions in response to a predetermined load pressure which imposes a shear stress on the fluid. (see ISO 1133) It will be appreciated that MFR is inversely related to viscosity.

In a simple test apparatus of the type commonly used to study molten polymers, the polymer is placed in a heated cylinder and downward pressure is applied to it by a piston of a known weight (eg 2.1 kg). An opening in the form of a die of known dimensions is provided at the base of the cylinder. The quantity Q grams of polymer which flows through the die in a given time (typically 10 mins) is then measured.

It will be appreciated that this system only provides a value of MFR (and therefore of viscosity) for a given shear stress. Since for such materials viscosity depends on shear stress, different values of MFR will be obtained if different weights are applied to the piston.

A more advanced arrangement is used in known on-line rheometers which are found in polymerisation plants. In these instruments a gear pump is provided to feed the fluid (i.e polymer melt) through a die of known dimensions. Transducers are provided to measure pressure at different locations within or near the die. During operation, the speed of the pump is adjusted such that a predetermined pressure drop over the die occurs. This preferably is chosen to be equivalent to the shear stress applied by the piston in the previously described apparatus. When the required pressure drop is obtained, the speed of the gear pump used to obtain that pressure is noted. This is used in combination with the known transport properties of the gear pump to provide the melt volume ratio (MVR) in terms of volume in cubic centimetres per 10 minutes. If the apparatus is not run at the exact shear stress equivalent referred to previously, then data obtained at other shear stresses is used as a basis for extrapolation. The MFR (in grams/10 min) can then be determined from the MVR by using the known density of the polymer melt.

The apparatus is termed "on-line" because the pump may be fed directly from a bypass leading from the extruder such that a polymer may be sampled during the operation of the extruder. In order to enable polymer to be returned to the extruder, the bypass may be in the form of a loop with a pump at either end of the rheometer and a further bypass loop with a pump is provided around the rheometer itself. This enables a flow of polymer to be directed to the rheometer as required whilst enabling the desired pressure drop to be created.

Another benefit of such an apparatus is that it is possible to measure MFR across a range of shear stresses such that a stress/viscosity curve may be produced. The shape of such a curve is indicative of the molecular weight distribution (MWD) of the polymer. (The molecular weight distribution is the distribution of the masses of the molecules forming the polymer.) Essentially, the lower the slope of the curve, the wider the MWD.

In comparatively simple applications, two points from the shear stress-viscosity curve may be determined using two transducers in the rheometer and the curve may be approximated to a straight line between them. If three transducers are available then a curve may be fitted empirically to the resulting data. In order to obtain a higher number of points, the speed of the pump may be varied to obtain a further set of readings. The resulting data may be fitted to a power law and the exponent is taken as characteristic of the MWD.

However, there are drawbacks with this approach. Firstly, due to limitations in the pressure transducers and in the capacity of gear pumps currently available, together with the need for short residence times, for low values of stress it is presently not possible to directly measure the MFR by applying the shear stress that is equivalent to MFR at a given weight. Consequently, it is necessary to make measurements using a higher shear stress and then to find the MFR by extrapolation. This is done using a power law function fitted to previously acquired measurements. Due to the non-Newtonian behaviour ("shear thinning") of polymers, the power law function does not provide a good fit to viscosity versus shear stress over wide ranges of shear rate. Thus, this procedure is inherently inaccurate. Furthermore, fitting viscosity versus shear stress to any given equation, whether it be a power law, a polynomial or rheological constitutive equation will inherently suffer from lack of fit. Thus, slope factors or any other fitted parameter will be inaccurate.

Finally, whilst data curves provided using a power law fit may be compared to previously obtained curves for the purpose of classification, this approach does not differentiate between different MWD's with sufficient accuracy.

Viewed from one aspect, the present invention provides a method of studying the properties of a fluid comprising the steps of:

a) providing a rheometer having a pump and a die arranged such that the pump may pump the fluid through the die, b) supplying the fluid to the rheometer, c) with the pump at one speed, obtaining value(s) indicative of the shear stress in the fluid within the die to obtain a set of data, and d) directly comparing the set of data with previously acquired data corresponding to a fluid with known Theological properties.

By "directly comparing" it is meant that the members of the sets of data are numerically compared, rather than attempting to fit the data to a function such as a power law and then comparing the resultant function to a function derived from previously acquired data.

In a simple case, the pump may only be run at a single speed and the set of data comprises value(s) from pressure transducer(s) associated with the die. However, preferably the invention further comprises repeating step c) at different constant pump speeds to obtain the set of data.

Thus, by means of this method, values indicative of the shear stress may be obtained for each of a range of different pump speeds. For example, at each speed a single pressure transducer may be used to determine pressure within the rheometer. In more advanced applications of the invention, a plurality of transducers (e.g. three) may be used.

The previously acquired data may be theoretically determined, but preferably it is derived from a sample of fluid known to have desired properties, preferably by performing steps (a) to (d) on such fluid. Data may also be obtained from fluid under a range of known conditions varying from the ideal and which therefore correspond to non-ideal product.

By determining whether the properties of the new fluid are sufficiently close to those of the previously acquired data it may be determined whether the properties of the fluid are acceptable. The data corresponding to non-ideal product may be used to determine why product is not acceptable.

In a simple case, with a sufficient number of different values obtained, a set of numbers which is characteristic of the particular fluid (for example a molten polymer) may be produced. This set may be compared with a corresponding set which is known to relate to acceptable products (e.g. from previously produced product). By determining whether the numbers are sufficiently similar (eg within previously specified tolerances) it may be determined whether the fluid is itself acceptable. It will be appreciated that these numbers relate to molecular weight and molecular weight distribution, although values need never be found for these parameters. Nevertheless, it may in practice be useful to do so.

The MFR obtained in the most basic prior art method represents only a single point in a shear stress-viscosity curve for a polymer. Furthermore, because the invention compares data directly, there is no attempt to fit a curve empirically to a set of data as is done with the more complex prior art methods. Thus, the introduction of errors which this incurs is avoided.

Indeed, there is not even any need for conversion of measured values into particular units and so, for example, figures of pump revolutions per minute and pressure transducer output in volts may be used. However, in many applications it may nevertheless be preferable to perform preliminary manipulation of the data. Additionally or alternatively data may be transformed into a suitable format for reading by associated software.

As discussed above, the previously acquired sets of data may have been obtained by making similar measurements of known polymers having desired characteristics. For example, sets of data may be obtained for each polymer which it is desired to produce corresponding to the ideal conditions for producing that polymer. Data may also optionally be produced for off-specification polymer.

If sufficient measurements are made at different pump speeds then a set of data will be obtained which can provide a "fingerprint" of the polymer concerned. Close similarity between the measured data and one of the previously acquired sets of data may then be used to identify the polymer concerned and/or to determine whether a desired polymer is being produced with the correct characteristics. Likewise, a match with an off-specification polymer may be used to determine what remedial action is required.

It will be appreciated that this comparison could be performed in numerous ways and in the simplest case useful information could be obtained even from visual comparisons of plots of the various data sets. However, these comparisons are preferably automated. In practice this means that the comparisons are carried out by a computer. In this way it is possible to provide information about the polymer at a speed only limited by the time needed to run the pump through its speed range.

Numerous known computational techniques may be used to perform the analysis, but it has been found that multivariate data analysis is particularly effective and accurate (see Martens and Naess 1989 "Multivariate Calibration" published by John Wiley). Thus, a latent variable corresponding to a best linear combination of the measured data may be introduced. The data are then redefined in relation to the latent variable.

In a particularly preferred form of the invention, Principal Component Analysis (PCA) of data from pressure transducers versus gear pump speed is used for classification of new samples in relation to old samples of known properties. The raw data may be subjected to preprocessing such as e.g. transformation, centring, smoothing or scaling. Subsequently, from a set of samples ("calibration set") of known properties a data subspace is empirically identified into which the sample data points may be projected. This subspace is described by a set of "latent variables", spanning individual axes in the subspace and is denoted the "model" of the given class of samples. The number of latent variables are then empirically found as those needed to give representative information related to flow properties of the fluid in question based on casual knowledge by the operator. It will be noted that it is not necessary to run any transformation to align with rheological parameters.

If a visual evaluation is desired (see below) a plot of the data may be produced where the axes are given by the latent variables, and where new samples are compared to the set of known samples, and to limiting values based on the same samples. For a mathematical evaluation (classification) upper and lower limiting values may be defined for the value of the latent variables, and for residuals of the raw data after projecting into the subspace an upper limiting value is defined. Then new samples may then be classified according to these limiting values.

Typically, when using PCA, the latent variables are defined by the eigenvectors of the (n×k) matrix where n is the number of samples in the calibration set, and k is the number of pressures being measured at given gear pump speeds. Each sample in the calibration set, and future process samples, may then be described by their score values along the individual latent variables.

By calculating the correlation of the latent variable with polymer property parameters like MWD, MFR, etc. one will obtain knowledge of along which direction these parameters have their largest variability in the latent variable data space. This information may be compared to the position of the individual samples in the same data space, to evaluate their score in relation to the different parameters.

By calculating the correlation of the latent variable with processing parameters like reactor temperature, reactor feed compositions etc., one will obtain knowledge of along which direction these parameters have their largest variability in the latent variable data space. This information may be compared to the position of the individual samples in the same data space, to evaluate their score in relation to the different parameters, and it may be used to estimate how process parameters should be changed to change the positioning of the product in the latent variable space to have the selected flow properties represented by the measured pressure values.

It is particularly preferred for the method to be implemented using a computer arranged to display a score plot representing the data at least substantially in real time. In this way, as new data is acquired and new plots are added to the score plot, changes in the fluid (polymer) characteristics may be followed. It is helpful for an indication to be provided on the display of where the boundaries between acceptable and unacceptable points lie, for example based on statistical quantities. The indications may be a boundary line in the form of an ellipse. Points falling outside the boundary correspond to unacceptable product.

As discussed above, the score may be evaluated in relation to different parameters and so it is possible to correlate the position of a point outside the boundary with the corresponding deficiency in its properties. This information may then be used to enable appropriate corrective action to be taken by a plant technician. For example, the previously acquired data sets could include data corresponding to known incorrect settings for the desired product from which previously determined corrective action may be taken. Such previous data sets could have been deliberately produced or they could be learned automatically from analysis of previous operations of the plant. Alternatively the plant may be adjusted in an iterative manner based upon the nature of the deviation of the measured data sets from the desired data set.

In particularly preferred forms of the invention, means is provided to automatically adjust the operating conditions of the plant in order to ameliorate the deficiency. Of course, there need not be a display for this to be effective—the "ellipse" may simply be a defined volume of data space.

Another advantage of this form of the invention is that even if product is determined to be acceptable, it is possible to monitor variations in where points are plotted (or located in data space) in order to determine trends which may; be used to anticipate future deficiencies and to take corrective action before they occur. Preferably this is also implemented automatically.

In this context PCA represents one way of identifying the latent variables. However, it will be appreciated that any other mathematical method involving linear or non-linear transformation of the pressure data into a set of latent variables may be used. Examples of other methods are Partial Least Squares Regression (PLSR), Neural Network (NN) description and curve fitting of the pressure data or preprocessed pressure data to a curve of selected exponential degree.

Another application of the invention is to use the pressure data for quantification of selected polymer properties, e.g. MFR or MWD. Again the raw data may be subject to preprocessing such as e.g. transformation, centring, smoothing or scaling. From a set of samples ("calibration set") of known properties it is then possible empirically to identify a mathematical relation (the "model") to quantify the selected properties based on the preprocessed pressure. This model may be any linear or non-linear relation defined by methods like Principal Component Regression (PCR), Partial Least Squares Regression (PLSR), Neural Network (NN), etc.

When using PCR and PLS, latent variables may be identified principally in the same way as with PCA (above), and then a linear regression model is developed between the polymer property and the selected latent variables. In the same way as when doing classification above, the score values in the latent variable space may then be used for visual and mathematical evaluation. Correlation between the latent variables and process parameters may be used to identify how the process parameters should be changed to adjust the selected property of the polymer being produced.

It will be appreciated from the foregoing that the present invention is useful in the field of polymer production and so the rheometer is preferably an on-line rheometer associated with an extruder used in such a context. Polymer may be fed from the extruder directly to the rheometer by means of a bypass in the known manner (discussed above). Because of the speed of operation and the improved accuracy of the method of the invention, if the properties of the polymer are as desired, this will be known much more speedily than in the prior art system. Furthermore, it is also possible to determine more quickly if the measured characteristics are not as required and then to adjust the operating conditions of the reactor accordingly in order to obtain the desired characteristics. Consequently, wasted production may be greatly reduced.

It is possible to apply the method of the present invention either only when the reactor is first set up for a given production run, or at occasional intervals as required by quality control. However, since the method may operate automatically it is particularly preferred that regular and comparatively frequent measurements be made, say around every 10 minutes.

Polymer producing plants are normally operated continuously and if it is desired to change from production of one polymer type or grade to another this is done without closing down the plant. Instead, the reactor operating conditions are adjusted in order to change the polymer thereby produced and fed to the extruder. Thus, preferably the method of the invention is used to obtain data which is used to monitor the transition between products. Since in the preferred forms of the invention the data acquisition and subsequent comparison steps are carried out by computer, this may be done rapidly. Consequently, the transition may be effected more smoothly and quickly than in the prior art and moreover the operator can determine more quickly when the desired product starts to be produced. Since polymerisation reactors produce tens of tonnes of material per hour, and the transition may take hours to complete, it will be appreciated that this significantly reduces the amount of wastage associated with operation of the reactor. Needless to say, this application of the invention may represent a significant advantage in terms of saving time and materials and thereby costs.

Sets of known data could be provided relating to the intermediate stages of such a transition from a first to a second polymer specification, e.g. based on previous successful transitions. However, it has been found to be highly effective for the measured data to be compared with data corresponding to the desired second polymer specification. Thus, when the measured values stabilise within a predetermined deviation from the stored data then it may be concluded that the product is close to the second polymer specification. If required, additional tests may then be carried out. The measured data may also be analysed with respect to time to determine trends.

Particularly when there are only comparatively small differences between the characteristics of the first and second polymer specifications then the transition may be monitored using the preferred forms of the invention discussed above. However, especially where the differences are greater, it is appropriate to apply the invention in a different manner.

In particular, due to the significant and comparatively rapid changes occurring to the product during such a transition, it has been found more effective to obtain smaller sets of data at more frequent intervals. Thus, it has been found effective to run the pump at a single speed, e.g. 4.5 rpm, preferably creating a continuous flow of polymer through the rheometer. Preferably the actual pump speed is selected depending on the characteristics (such as viscosity) of the polymer. Data may then be measured either continuously or, more preferably, at intervals of say 2–10 seconds, eg about every 5 seconds.

As known rheometers have typically three transducers, it is convenient to form sets of data from simultaneous measurements from each, as previously discussed. However, in many applications it is satisfactory if only a single transducers output is measured.

It is believed that this method is in itself inventive and therefore, viewed from a further aspect, the invention provides a method of monitoring a transition from a first specification of product to a second specification of product in a polymerisation process wherein polymer from the process is repeatedly or continuously supplied to a rheometer during the transition and data from the rheometer is repeatedly or continuously compared to known data to determine approximately when the transition is completed.

The method is preferably carried out as set forth above. Thus, one, two, three or more output values from the rheometer are taken at short intervals and compared to the corresponding values for the second specification of product. It may be determined that the transition has approximately been completed when the measured values stabilise within a predetermined deviation from the known data. For example, the predetermined deviation may be two standard deviations and stabilisation may be determined when this "target" is met for a given continuous period of time.

It has been found that this preferred arrangement is highly effective and can significantly reduce wastage because the comparative simplicity of the measurements used means that they can be carried out almost in real time. Thus, the operator discovers much more quickly when the new specification is reached. Moreover, it has been found that the invention provides a surprisingly accurate determination of the state of the transition. However, it is preferably supplemented by conventional rheology tests when it is determined that the transition is approximately complete.

A further advantage follows from the fact that conventional rheometry techniques are difficult to apply during a transition. This is because it is generally not known what material is being produced at a given time and so the usual calibrations and correlations are not applicable. The technique discussed above completely avoids such problems.

The invention also extends to an apparatus for operating in a manner first discussed above and therefore viewed from a further aspect the invention provides an apparatus for studying the properties of a fluid comprising:

a) a rheometer having a pump and a die arranged such that the pump may pump the fluid through the die, b) means for supplying the fluid to the rheometer, c) means for obtaining value(s) indicative of the shear stress in the fluid within the die to obtain a set of data, and d) means for directly comparing the set of data with previously acquired data corresponding to a fluid with known rheological properties.

Preferably the means of part (c) obtain the value(s) at different constant pump speeds.

The operation of the apparatus is preferably as previously described.

The invention also extends to an apparatus for carrying out the invention secondly described above and so viewed from a still further aspect, the invention provides an apparatus for monitoring a transition from a first specification of product to a second specification of product in a polymerisation process comprising a rheometer to which polymer from the process may be repeatedly or continuously supplied during the transition and means for receiving data from the rheometer such that the data may be repeatedly or continuously compared to known data to determine approximately when the transition is completed.

Furthermore, the invention also extends to a polymer production plant incorporating the methods or apparatuses of the invention as set forth above. Thus, such a plant may be controlled based upon the output from the methods and apparatuses. This can be by means of manual control inputs based upon the output data and/or by automatic control using signals derived from the output data. The invention also extends to polymer products thereby produced.

An embodiment of the invention will now be described, by way of example only, and with reference to the accompanying drawings.

Figure 1:
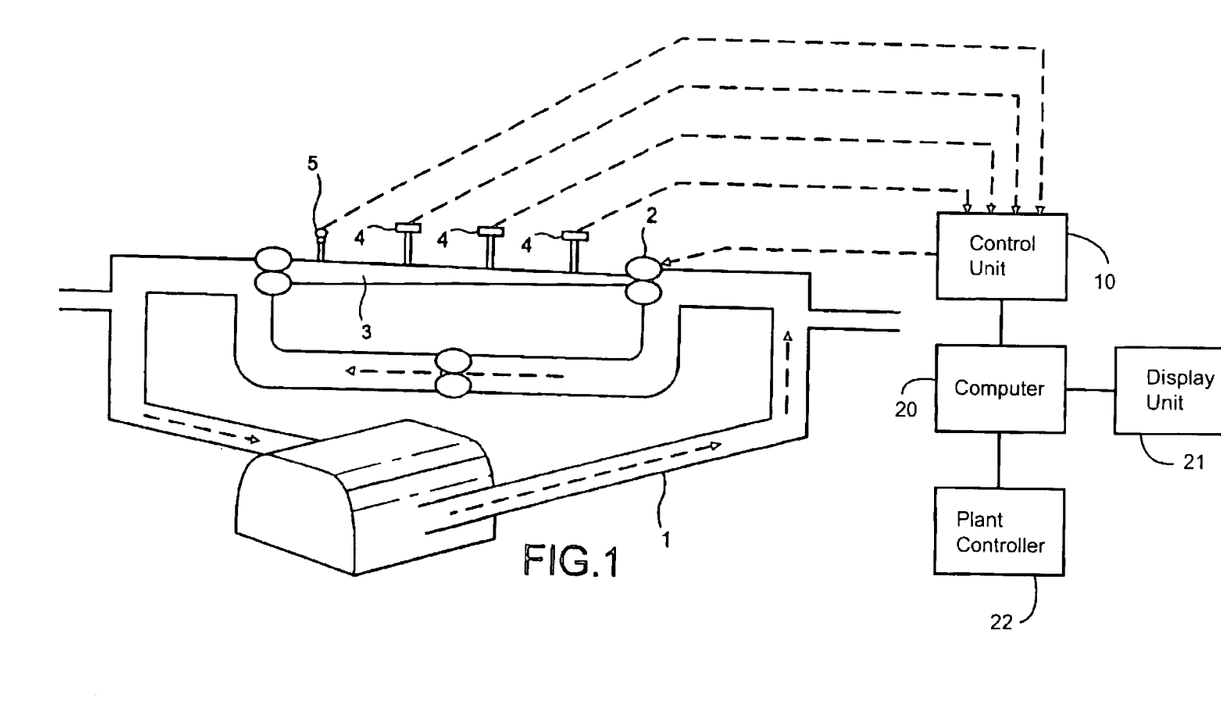
FIG. 1 is a schematic view of a rheometer.

FIG. 1 illustrates a rheometer which is essentially of known design. This is a Gøottfert real time spectrometer type RTS92.93 EEx 019.06.0 Model A/A. The rheometer is fed by means of a bypass from an appropriate part of a polymer extruder.

As may be seen from the figure, the fluid enters the rheometer via conduit 1 from where it is pumped by means of gear pump 2 through wedge die 3. Three pressure transducers 4 are located at different positions within the wedge die in order to measure the pressure within the fluid at their appropriate locations. In addition, a thermocouple 5 is provided for determining the temperature of the polymer.

Also provided is a control unit 10 which is connected to the gear pump, the pressure transducers and the thermocouple. Signals from the control unit are used to adjust the speed of the gear pump as required and signals from the pressure transducers and thermocouple are recorded During operation of the extruder, either continuously or discontinuously at predetermined intervals, molten polymer is fed to the rheometer. At predetermined intervals, a measurement sequence is initiated. The gear pump 2 is first operated at a first speed near the lower end of its operating range in order to force the polymer through the die 3. Because of the viscoelastic nature of the polymer, it takes some time for the flow to become steady. The control software therefore applies pre-determined criteria to determine when stable conditions have been reached. When this occurs data from the pressure transducers is recorded by the control unit. The pump speed is then increased and a further set of pressure values obtained in the same manner. This process is then repeated as often as required. Typically around eight such values will be obtained over a period about 10 minutes.

Thus it will be seen that a set of, in this case, 24 pressure data are acquired corresponding to eight pump speeds. The data may then be centred or weighted and then transposed into the correct format for subsequent processing. It is then fed to a computer 20 where the data is compared with previously acquired data sets which form models. This is carried out using multivariate analysis. Models for a given product are based on data collected from several campaigns. In such a model, each point represents data obtained from five to eight rheometer tests.

The computer is associated with a display unit 21 which displays a scatterplot representing the results of the analysis. The computer is also connected to the plant controller 22. This enables the plant operating conditions to be varied as required in response to the computer analysis.

Figure 2:
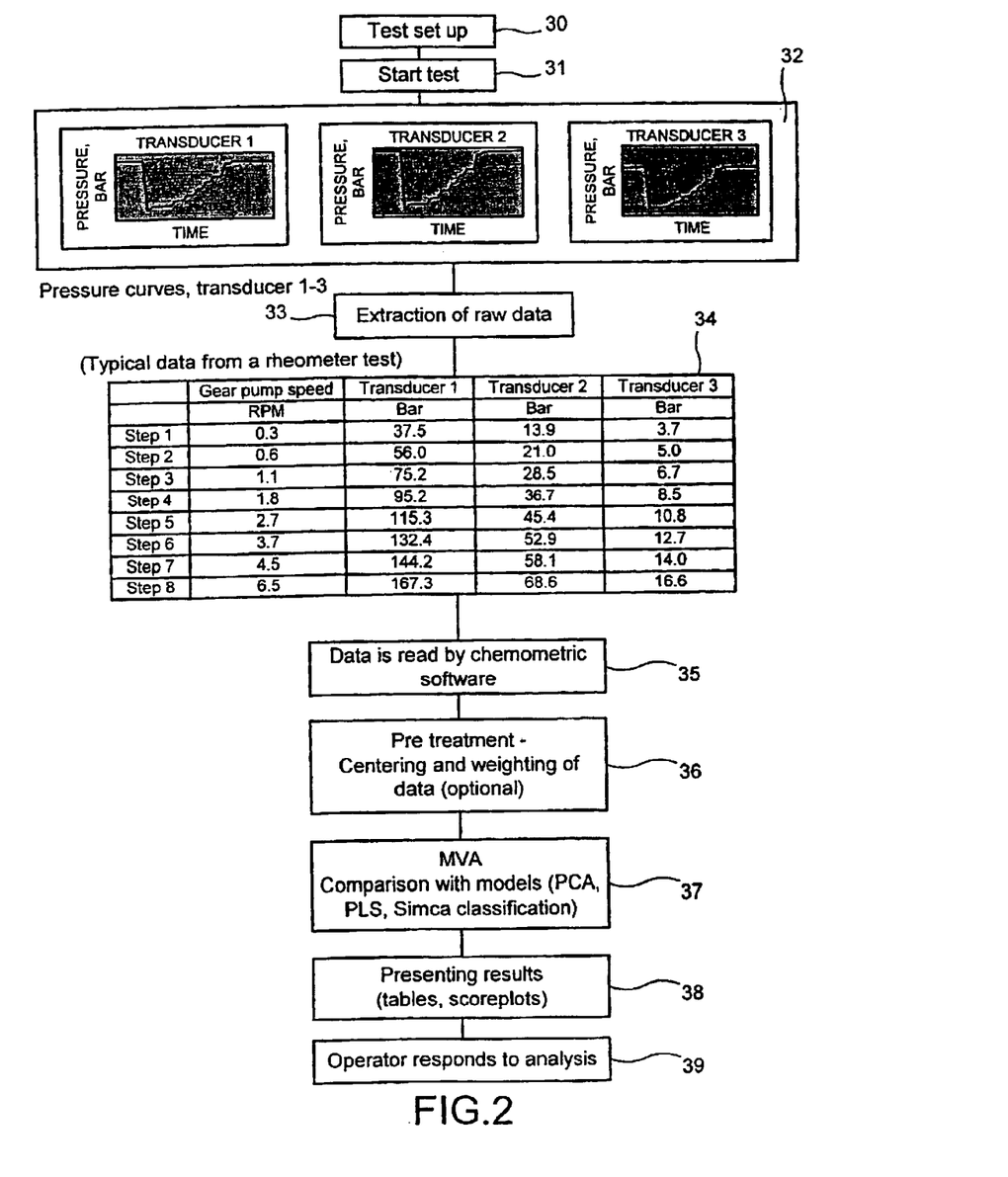
FIG. 2 is a flow chart describing the operation of one embodiment of the invention.

The operation of the system and in particular the comparison steps are now described in more detail with reference to FIG. 2 which is a flow chart.

Firstly (box 30) the initial conditions for the first test are established. Once this is done, the test is started (box 31). The gear pump is then run through a range of speeds as previously discussed and a set of data representing transducer-detected pressure versus time are collected (box 32). As the pump speed varies with time, raw data comprising a set of three transducer pressures for each different pump speed is obtained (box 33). Box 34 contains an example of such data.

The data is then read (box 35) by chemometric software, this step optionally includes pre-treatment such as centring and weighting (box 36). The data then undergoes multivariate analysis (box 37) whereby it is compared to models and the results are then presented as tables and/or scatter plots (box 38). Finally, this data is read by an operator who may respond to correct any determined deficiency. (Alternatively, this step may be automated).

Figure 5:
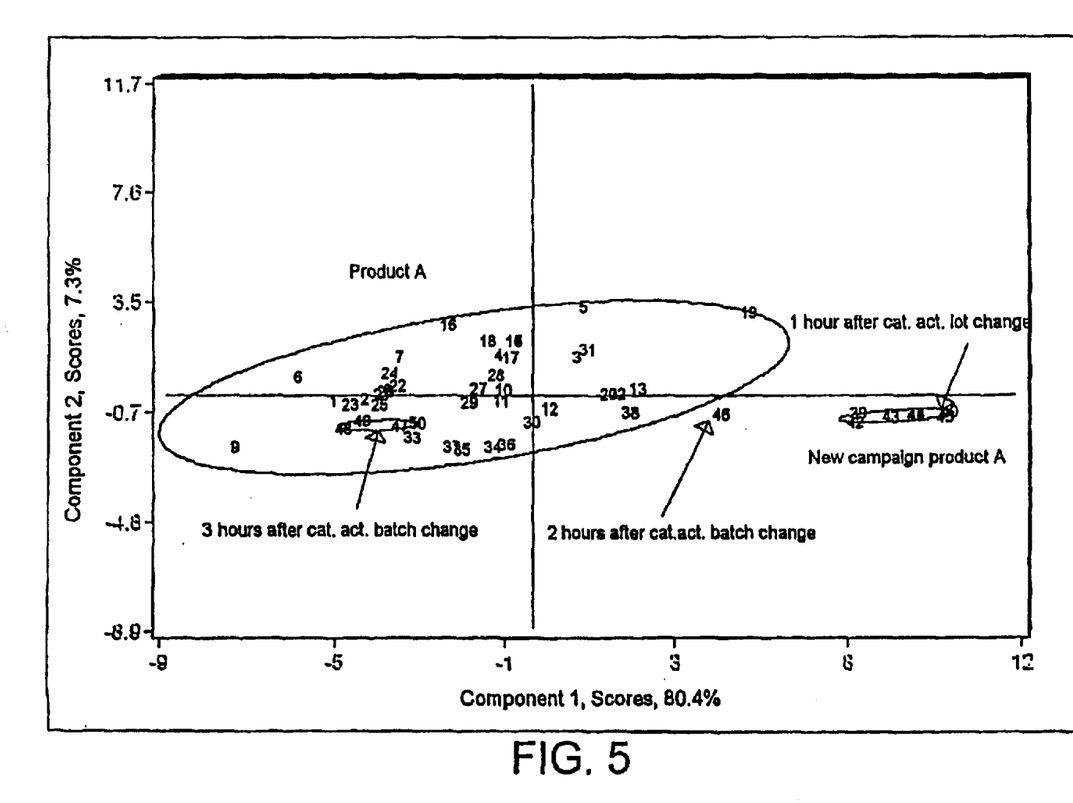

FIG. 5 which is discussed more fully below, is an example of a scatterplot of the results of the above analysis. The large ellipse represents the normal variation of properties for a given polymer. The basic principle is that if the result of the analysis is that the point representing the new data falls within the desired ellipse then the characteristics of the product are as required. Thus, points 9, 6, 7, 28 etc represent on-specification product. Point 46, however, represents product which falls outside the derived specification. When this occurs, the plant may be adjusted accordingly, either by a technician or automatically via the link from the computer 20 and the plant controller.

Figure 7:
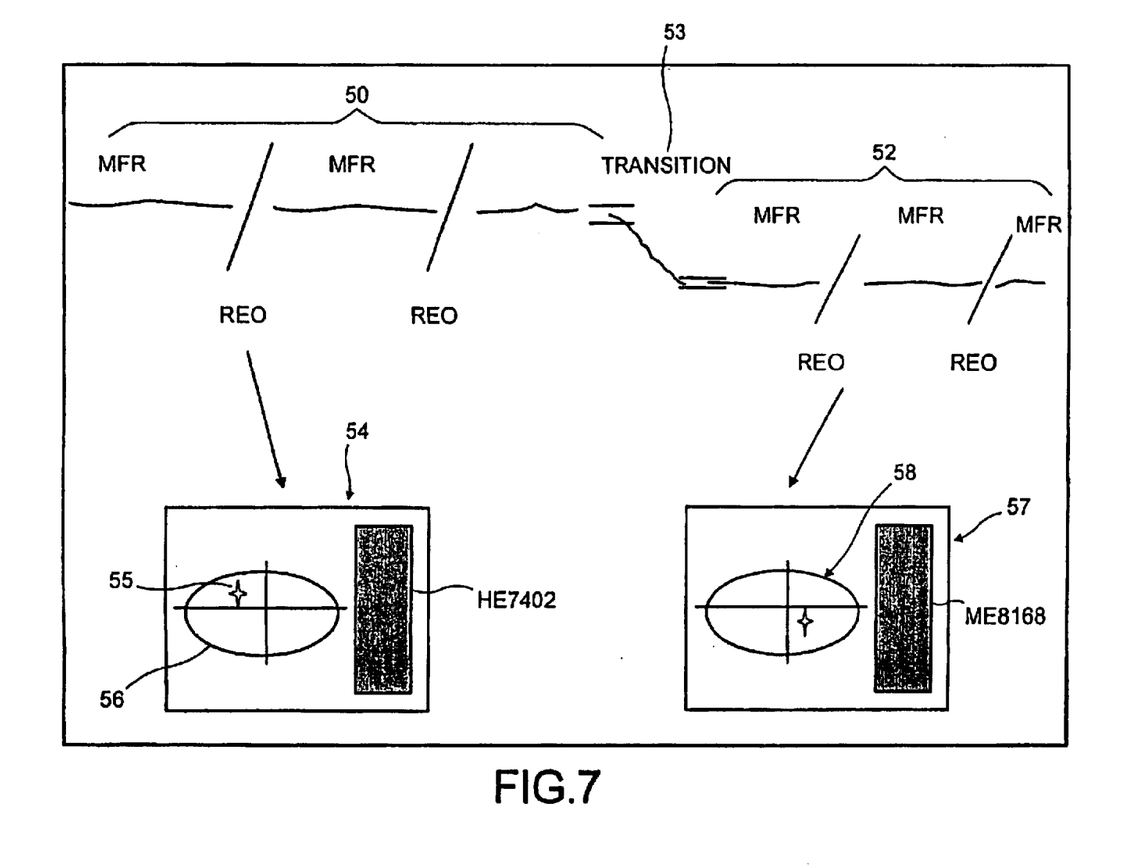
FIG. 7 is a schematic diagram illustrating the use of the invention before, during and after a transition.

FIG. 7 gives an overview of the use of the invention before, during and after a transition in combination with conventional MFR measurements.

As may be seen from the upper part of the figure, a first grade of polymer is initially produced (generally at reference 50). Whilst this is produced, conventional MFR measurements are taken, interspersed by measurements according to the invention (REO). The latter comprise obtaining a full set of data at a range of pump speeds from all three transducers on the rheometer (FIG. 1) as discussed above, together with the analysis illustrated in FIG. 2. This provides the output shown at 54 where the product is shown to be within specification for the first grade by the marker 55 falling within ellipse 56.

A similar regime of measurement is carried out during the production of the second grade of polymer (generally at reference 52). The REO tests result in output such as 57 showing the product to be within the new specification represented by ellipse 58.

During the grade transition 53, a different regime is applied. The rheometer pump is run at a continuous speed of 4.5 rpm and the output from a single transducer is measured every 5 seconds. This is then compared to the stored data comprising the transducer value for the second grade of polymer. When it has stabilised within two standard deviations of that value it may be concluded that the product is at least approximately within the specification of the second grade, at which point the MFR and REO tests may resume. Conventional quality control tests are also carried out.

EXAMPLE 1

Improved Product Consistency by an Off-Line Use of the System

Figure 3:
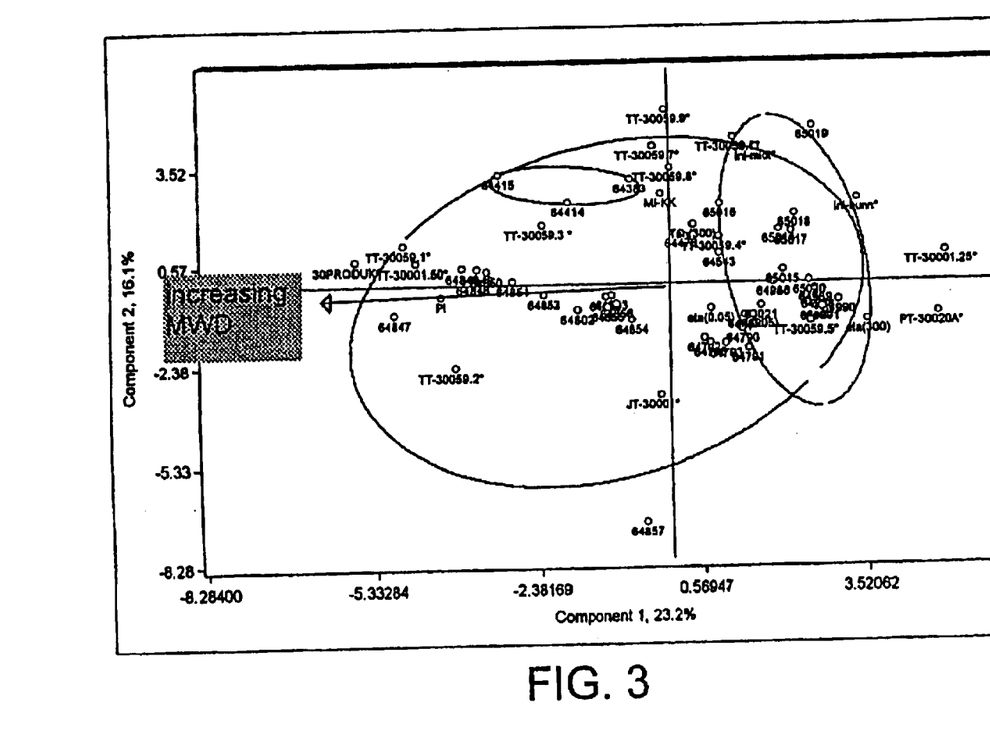
FIGS. 3 to 6 are various plots relating to the invention.

In this example multivariate analysis (MVA) of rheometer and process data has been used to relate changes in MWD to reactor parameters. FIG. 3 shows a graphical representation of a partial least squares (PLS) model (scores and loadings plot according to the methodology of MVA: PCA and PLS, see Martens and Naess). As may be seen from FIG. 3, the variation on MWD in relation to the two components is indicated with an arrow. Thus, points towards the left of the graph relate to product with higher MWD.

It will be appreciated that if the MWD is found to be too high, the plant controller can then remedy this in the conventional manner. Controlling the polymerisation process according to the relationships presented graphically in FIG. 3 has achieved a reduced variability of the product as displayed in the scoreplot based on rheometer data on produced lots (FIG. 4).

Figure 4:
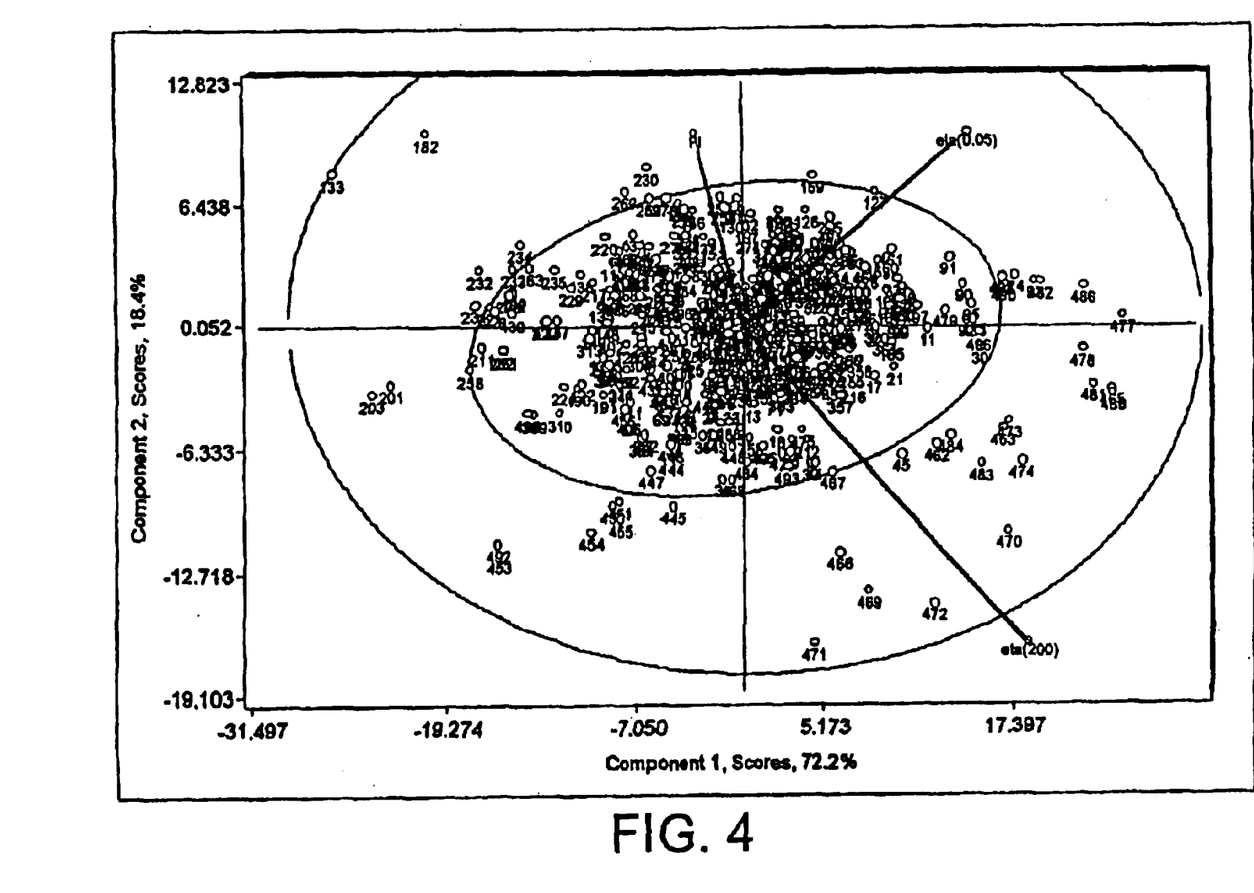

FIG. 4 displays a crossplot of scores in the first two latent variables from a principal component analysis (PCA) of rheometer data. Each data point represents one measurement of one lot from the plant. A study of the covariances in the model tell us that the variation in MW is mainly along the x-axis while variation in MWD is along the y-axis. The outer circle in FIG. 4 shows the observed variation of the product before application of the methodology of the invention. The product variation was characterised with less control of the MWD (variation along vertical axis) and larger variation in MW (along horizontal axis). After implementing the new methodology the product variation are reduced to the inner ellipse in FIG. 4.

EXAMPLE 2

Effect of Changing Catalyst Activation Batch During Production

This example is from a polyethylene polymer production plant where the rheometer is located on an extruder and the time lag between reactor and the rheometer could be up to two hours depending on process conditions.

In this case the MVA model consists of data from several production campaigns and FIG. 5 shows transition towards product A. In the scoreplot the large ellipse (no. 1–no. 38) represents the model and the small ellipse (no. 39–no. 44) represents the new campaign. Also shown is the transition from the off-specification material (no. 44, no. 45) back to on-specification material (no. 47–no. 50).

The model consists of lot samples while the new campaign is rheometer data with approximately 1 hour interval. It can be seen from the scatterplot that the samples from the new campaigns fall outside the predefined model. This is according to the model due to a more narrow MWD as may be seen by the displacement to the right.

Changes in the process were initiated in the known manner in order to bring production back to on-specification materials. One of the initiatives was to change catalyst activation batch. The resulting location in the score plot is shown 1, 2 and 3 hours after the change was initiated. Location in the scoreplot is a clear response to changes in process conditions reflecting time after change of catalyst batch. As may be seen, production was brought back to on-specification material properties.

Figure 6:
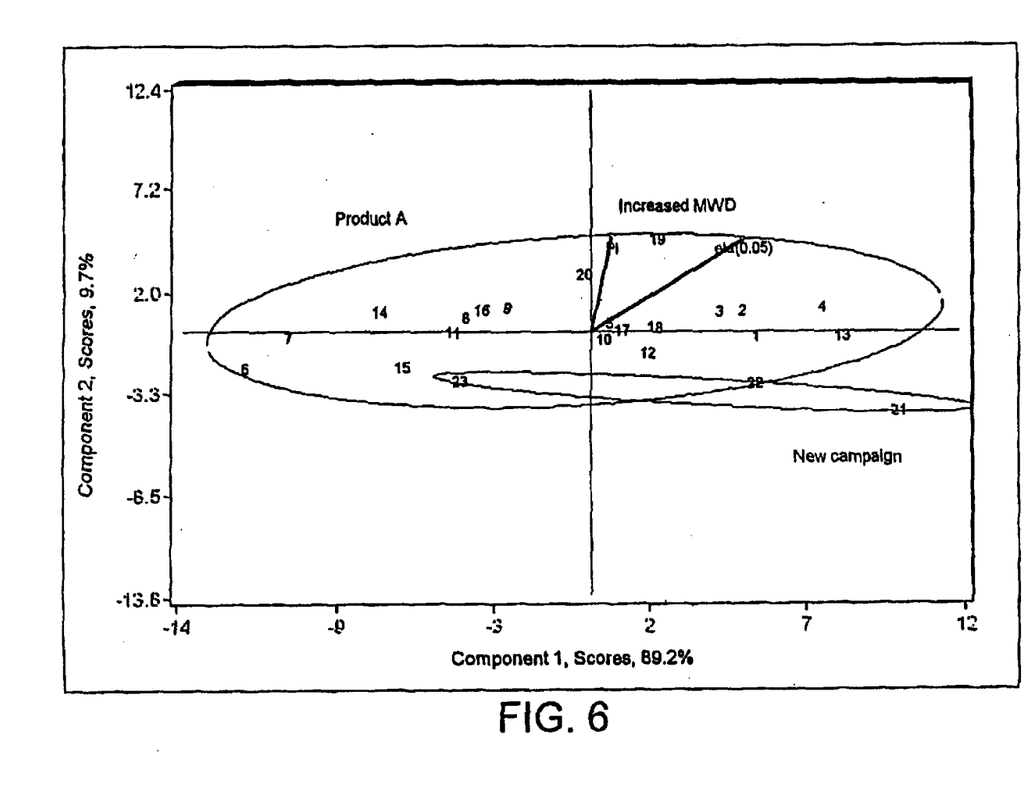

Some samples from the on-line model and some lots from the transition were later analysed using an off-line rheometer. A plot of score values from the first and second latent variables (see Martens and Naess) from the PCA analysis shows the same trend as the on-line data. In FIG. 6 the sample marked 21–23 is from the new campaign and is produced before, during and after catalyst activating lot change.

Variation along the horizontal axis is in this case related to Molecular weight (MW) and variation along the vertical axis is related to molecular weight distribution (MWD). In FIG. 6 this is indicated with the polydispersity index, PI. Off-line analysis verifies the interpretation of the on-line data.

What is claimed is:

1. A method comprising:
   a) providing a rheometer having a pump and a die arranged such that the pump may pump a fluid through the die,
   b) supplying the fluid to the rheometer,
   c) with the pump at one speed, obtaining value(s) indicative of the shear stress in the fluid within the die to obtain a set of data, and
   d) directly comparing the set of data with previously obtained data corresponding to a fluid with known rheological properties.

2. A method as claimed in claim 1, further comprising: repeating step c) at different constant pump speeds to obtain the set of data.

3. A method as claimed in claim 1, wherein the comparing is performed using multivariate data analysis.

4. A method as claimed in claim 1, wherein the fluid is a molten polymer and the rheometer is an on-line rheometer associated with a polymer production plant.

5. A method as claimed in claim 4, wherein if the polymer characteristics are not acceptable, the operating conditions of the plant are adjusted accordingly.

6. A method as claimed in claim 5, wherein the adjustment of the plant occurs automatically.

7. A method as claimed claim 4, wherein the method is repeated at regular intervals during the operation of the plant.

8. A method as claimed in claim 4, wherein the plant operating conditions are adjusted in order to change the polymer thereby produced and the data is used to monitor the transition between products.

9. A method of producing an extruded polymer, wherein the method comprises the method according to claim 1.

10. A method according to claim 1, further comprising the step of using the results of the comparing in step (d) to quantify a selected property of the fluid.

11. A method as claimed in claim 10, wherein the property is Melt Flow Rate or Molecular Weight Distribution.

12. A polymer production plant operating according to the method of claim 1.

13. Polymer product produced by a method comprising the method of claim 1.

14. An apparatus comprising:
   a) a rheometer having a pump and a die arranged such that the pump may pump a fluid through the die,
   b) means for supplying the fluid to the rheometer,
   c) means for obtaining value(s) indicative of the shear stress in the fluid within the die to obtain a set of data, and
   d) means for directly comparing the set of data with previously obtained data corresponding to a fluid with known rheological properties.

15. An apparatus as claimed in claim 14, wherein the means of part (c) is arranged to obtain the values indicative of shear stress at different constant pump speeds.

16. A polymer production plant comprising the apparatus as claimed in claim 14.

17. A method of monitoring a transition from a first specification of product to a second specification of product in a polymerisation process wherein polymer from the process is repeatedly or continuously supplied to a rheometer during the transition and data from the rheometer is repeatedly or continuously directly compared to known data to determine approximately when the transition is completed.

18. A method as claimed in claim 17, wherein output values from one, two, three or more transducers in the rheometer are taken at short intervals and the known data comprises previously acquired corresponding values for the second specification of product.

19. A method as claimed in claim 18, wherein it is determined that the transition has approximately been completed when the measured values stabilise within a predetermined deviation from the known data.

20. A method as claimed in claim 19, wherein the predetermined deviation corresponds to two standard deviations.

21. A method as claimed in claim 18, wherein the output values are taken every 2–10 seconds.

22. A method as claimed in claim 17, wherein the rheometer pump is operated at a constant speed whilst the data is acquired.

23. An apparatus for monitoring a transition from a first specification of product to a second specification of product in a polymerisation process comprising a rheometer to which polymer from the process may be repeatedly or continuously supplied during the transition and processing means for receiving data from the rheometer, the processing means being arranged to repeatedly or continuously directly compare the data from the rheometer to known data to determine approximately when the transition is completed.

24. An apparatus as claimed in claim 23, wherein the processing means comprises electronic computing apparatus.

25. A method of controlling a manufacturing process comprising:
   a) providing a rheometer having a pump and a die arranged such that the pump pumps a fluid through the die,
   b) with the pump at one speed, obtaining value(s) indicative of the shear stress in the fluid within the die to obtain a set of data,
   c) directly comparing the set of data with previously obtained data corresponding to a fluid with known rheological properties, and
   d) controlling the manufacturing process based on the comparing.

26. An apparatus comprising:
   a) a rheometer having a pump and a die arranged such that the pump pumps a fluid through the die,
   b) one or more transducers for obtaining value(s) indicative of the shear stress in the fluid within the die to obtain a set of data, and
   c) a processor for directly comparing the set of data with previously obtained data corresponding to a fluid with known rheological properties.

27. An apparatus for monitoring a transition from a first specification of product to a second specification of product in a polymerisation process comprising a rheometer to which polymer from the process may be repeatedly or continuously supplied during the transition and a processor for receiving data from the rheometer, the processor being arranged to repeatedly or continuously directly compare the data from the rheometer to known data to determine approximately when the transition is completed.

* * * * *